United States Patent
Berneth et al.

(10) Patent No.: US 6,835,725 B2
(45) Date of Patent: Dec. 28, 2004

(54) OPTICAL DATA CARRIER COMPRISING A CYANINE DYE AS LIGHT-ABSORBENT COMPOUND IN THE INFORMATION LAYER

(75) Inventors: Horst Berneth, Leverkusen (DE); Friedrich-Karl Bruder, Krefeld (DE); Wilfried Haese, Odenthal (DE); Rainer Hagen, Leverkusen (DE); Karin Hassenrück, Düsseldorf (DE); Serguei Kostromine, Swisttal (DE); Peter Landenberger, Köln (DE); Rafael Oser, Krefeld (DE); Thomas Sommermann, Bergisch Gladbach (DE); Josef-Walter Stawitz, Odenthal (DE); Thomas Bieringer, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 47 days.

(21) Appl. No.: 10/101,793

(22) Filed: Mar. 20, 2002

(65) Prior Publication Data

US 2003/0008234 A1 Jan. 9, 2003

(30) Foreign Application Priority Data

Mar. 28, 2001 (DE) .......................... 101 15 227
Jul. 25, 2001 (DE) .......................... 101 36 064
Jan. 24, 2002 (DE) .......................... 102 02 571

(51) Int. Cl.$^7$ .................. A61K 31/33; A61K 31/41; C07D 285/00; C07D 277/00; C07D 209/00
(52) U.S. Cl. ................ 514/183; 514/365; 514/363; 514/396; 514/408; 514/415; 548/136; 548/138; 548/146; 548/400; 548/452; 548/469
(58) Field of Search .................. 514/183, 365, 514/363, 396, 408, 415; 548/136, 138, 146, 400, 452, 469

(56) References Cited

U.S. PATENT DOCUMENTS

| | | | |
|---|---|---|---|
| 2,476,525 A | | 7/1949 | Anish et al. ............... 260/240 |
| 2,504,468 A | * | 4/1950 | Thompson ................ 548/121 |
| 3,071,467 A | | 1/1963 | Rauch ...................... 96/106 |
| 3,090,782 A | | 5/1963 | Coenen et al. .......... 260/240.6 |
| 3,287,465 A | | 11/1966 | Brack et al. ............... 260/305 |
| 4,751,309 A | | 6/1988 | Daltrozzo et al. ......... 546/176 |
| 5,266,699 A | | 11/1993 | Naef et al. ............... 546/61 |
| 6,214,431 B1 | | 4/2001 | Hua et al. ................ 428/64.1 |

FOREIGN PATENT DOCUMENTS

| | | |
|---|---|---|
| DE | 883 025 | 7/1953 |
| EP | 0 887 202 | 12/1998 |

(List continued on next page.)

OTHER PUBLICATIONS

Chemical Abstract DN 107:124468, also cited as JP 61282834.*

(List continued on next page.)

*Primary Examiner*—Richard L. Raymond
*Assistant Examiner*—Sudhaker B. Patel
(74) *Attorney, Agent, or Firm*—Godfried K. Akorli; Diderico van Eyl; Jill Denesvich

(57) ABSTRACT

Optical data carrier comprising a preferably transparent substrate which may, if desired, have previously been coated with one or more reflection layers and to whose surface a light-writeable information layer, if desired one or more reflection layers and if desired a protective layer or a further substrate or a covering layer have been applied, which can be written on or read by means of blue, red or infrared light, preferably laser light, where the information layer comprises a light-absorbent compound and, if desired, a binder, characterized in that at least one cyanine dye is used as light-absorbent compound.

10 Claims, 2 Drawing Sheets

FOREIGN PATENT DOCUMENTS

| | | |
|---|---|---|
| EP | 1 178 083 | 2/2002 |
| GB | 785939 | 2/1956 |
| GB | 848016 | 7/1958 |
| GB | 1024486 | 8/1963 |
| JP | 61282834 | * 12/1986 |
| JP | 6-336086 | 12/1994 |
| JP | 8-191171 | 7/1996 |
| JP | 2-557335 | 11/1996 |
| JP | 9-50629 | 2/1997 |
| JP | 10-58828 | 3/1998 |
| JP | 10-181206 | 7/1998 |
| JP | 11-43481 | 2/1999 |
| WO | 9917284 | * 4/1999 |

OTHER PUBLICATIONS

Chemical Abstract Dn 44:48859, also cited as U.S.P. 2504456.*

Roczniki Chemii Ann. Soc. Chim. Polonorum 37, 225 (month unavailable) 1963, Luminescencja.

Barwnikow Uczulajacych. I. Wpeyw Struktury Barwnika Na Jego Luminescencje by Kazimierz Kiciak.

J. Chem. Soc., (month unavailable) 1951, pp 1087–1092, Synthetic Long–Chain.

Aliphatic Compounds. Part IV. Some Methyl–substituted Oleic Acids by D. E. Ames and R. E. Bowman.

* cited by examiner

OPTICAL DATA CARRIER COMPRISING A CYANINE DYE AS LIGHT-ABSORBENT COMPOUND IN THE INFORMATION LAYER

The invention relates to a write-once optical data carrier comprising a cyanine dye as light-absorbent compound in the information layer, to a process for its production and also to the application of the above-mentioned dyes to a polymer substrate, in particular polycarbonate, by spin coating or vapour deposition.

Write-once optical data carriers using specific light-absorbent substances or mixtures thereof are particularly suitable for use in high-density writeable optical data stores which operate with blue laser diodes, in particular GaN or SHG laser diodes (360–460 nm) and/or for use in DVD-R or CD-R disks which operate with red (635–660 nm) or infrared (780–830 nm) laser diodes.

The write-once compact disk (CD-R, 780 nm) has recently experienced enormous volume growth and represents the technically established system.

The next generation of optical data stores—DVDs—is currently being introduced onto the market. Through the use of shorter-wave laser radiation (635–660 nm) and higher numerical aperture NA, the storage density can be increased. The writeable format in this case is DVD-R.

Today, optical data storage formats which use blue laser diodes (based on GaN, JP 08 191 171 or Second Harmonic Generation SHG JP 09 050 629) (360nm –460 nm) with high laser power are being developed. Writeable optical data stores will therefore also be used in this generation. The achievable storage density depends on the focussing of the laser spot on the information plane. Spot size scales with the laser wavelength $\lambda$/NA is the numerical aperture of the objective lens used. In order to obtain the highest possible storage density, the use of the smallest possible wavelength $\lambda$ is the aim. At present 390 nm is possible on the basis of semiconductor laser diodes.

The patent literature describes dye-based writeable optical data stores which are equally suitable for CD-R and DVD-R systems (JP-A 11 043 481 and JP-A 10 181 206). To achieve a high reflectivity and a high modulation height of the read-out signal and also to achieve sufficient sensitivity in writing, use is made of the fact that the IR wavelength of 780 nm of CD-Rs is located at the foot of the long wavelength flank of the absorption peak of the dye and the red wavelength of 635 nm or 650 nm of DVD-Rs is located at the foot of the short wavelength flank of the absorption peak of the dye. In JP-A 02 557 335, JP-A 10 058 828, JP-A 06 336 086, JP-A 02 865 955, WO-A 09 917 284 and U.S. Pat. No. 5,266,699, this concept is extended to the 450 nm working wavelength region on the short wavelength flank and the red and IR region on the long wavelength flank of the absorption peak.

Apart from the abovementioned optical properties, the writeable information layer comprising light-absorbent organic substances has to have a substantially amorphous morphology to keep the noise signal during writing or reading as small as possible. For this reason, it is particularly preferred that crystallization of the light-absorbent substances be prevented in the application of the substances by spin coating from a solution, by vapour deposition and/or sublimation during subsequent covering with metallic or dielectric layers under reduced pressure.

The amorphous layer comprising light-absorbent substances preferably has a high heat distortion resistance, since otherwise further layers of organic or inorganic material which are applied to the light-absorbent information layer by sputtering or vapour deposition would form blurred boundaries due to diffusion and thus adversely affect the reflectivity. Furthermore, a light-absorbent substance which has insufficient heat distortion resistance can, at the boundary to a polymeric support, diffuse into the latter and once again adversely affect the reflectivity.

A light-absorbent substance whose vapour pressure is too high can sublime during the above-mentioned deposition of further layers by sputtering or vapour deposition in a high vacuum and thus reduce the layer thickness to below the desired value. This in turn has an adverse effect on the reflectivity.

It is therefore an object of the invention to provide suitable compounds which satisfy the high requirements (e.g. light stability, favourable signal/noise ratio, damage-free application to the substrate material, and the like) for use in the information layer in a write-once optical data carrier, in particular for high-density writeable optical data store formats in a laser wavelength range from 340 to 830 nm.

Surprisingly, it has been found that light-absorbent compounds selected from the group of cyanine dyes can satisfy the abovementioned requirement profile particularly well.

Figure 1:
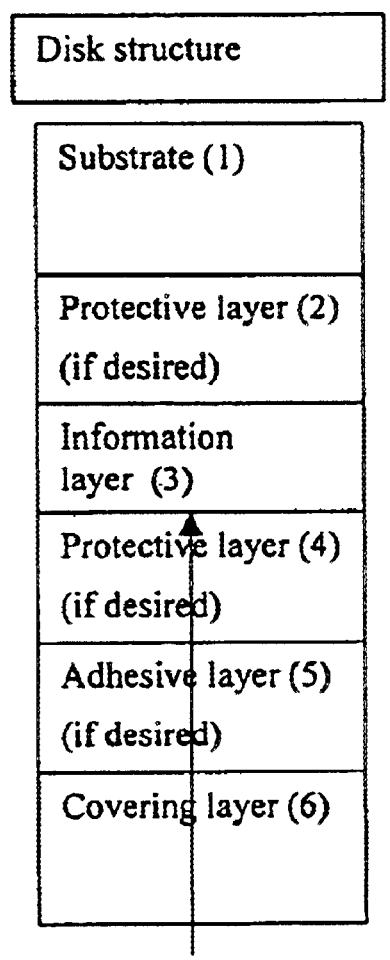
FIG. 1 Illustrates an optical data carrier with a layer structure of a transparent substrate, if desired a protective layer, an information layer, if desired a protective layer, if desired an adhesive layer, a covering layer.

The invention accordingly provides an optical data carrier comprising a preferably transparent substrate which may, if desired, have previously been coated with one or more reflection layers and to whose surface a light-writeable information layer, if desired one or more reflection layers and if desired a protective layer or a further substrate or a covering layer have been applied, which can be written on or read by means of blue, red or infrared light, preferably laser light, where the information layer comprises a light-absorbent compound and, if desired, a binder, characterized in that at least one cyanine dye is used as light-absorbent compound.

The light-absorbent compound should preferably be able to be changed thermally. The thermal change preferably occurs at a temperature of <600° C., particularly preferably at a temperature of <400° C., very particularly preferably at a temperature of <300° C., in particular <200° C. Such a change can be, for example, a decomposition or chemical change of the chromophoric centre of the light-absorbent compound.

Preference is given to a cyanine dye of the formula (I)

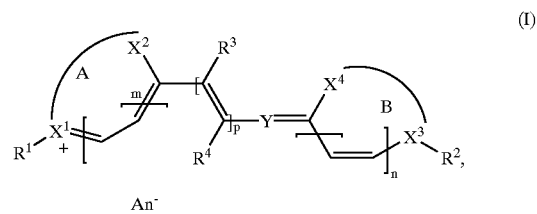

where
$X^1$ and $X^3$ represent nitrogen or $X^1$—$R^1$ and $X^3$—$R^2$ represent, independently of one another, S, $X^2$ represents O, S, N—$R^6$, $CR^8$ or $CR^8R^9$, $X^4$ represents O, S, $CR^{10}$ or N—$R^7$, Y represents N or C—$R^5$, $R^1$, $R^2$, $R^6$ and $R^7$ represent, independently of one another, $C_1$–$C_{16}$-alkyl, $C_3$–$C_6$-alkenyl, $C_5$–$C_7$-cycloalkyl or $C_7$–$C_{16}$-aralkyl, $R^3$, $R^4$ and $R^5$ represent, independently of one another, hydrogen, $C_1$–$C_{16}$-alkyl or cyano or $R^1$ and $R^3$ together represent a —$(CH_2)_2$—, —$(CH_2)_3$— or —$(CH_2)_4$— bridge when m=0 and p>0 or $R^{1\ and\ R5}$ together represent a —$(CH_2)_2$—, —$(CH_2)_3$— or —$(CH_2)_4$— bridge when m=0 and p=0 or $R^2$ and $R^5$ together represent a —$(CH_2)_2$—, —$(CH_2)_3$— or —$(CH_2)_4$— bridge when n=0, $R^8$, $R^9$ and $R^{10}$ represent, independently of one another, hydrogen or $C_1$–$C_{16}$-alkyl or $CR^8R^9$ represents a bivalent radical of the formula where the two bonds go out from the ring atom marked with an asterisk (*), m and n represent, independently of one another, 0 or 1, p represents 0, 1 or 2, the ring A including $X^1$, $X^2$ and the radical connecting $X^1$ and $x^2$ and the ring B including $X^3$, $X^4$ and the radical connecting $X^3$ and $X^4$ each represent, independently of one another, a five- or six-membered aromatic or pseudoaromatic or partially hydrogenated heterocyclic ring which may contain from 1 to 4 heteroatoms and/or be benzo- or naphtho-fused and/or be substituted by nonionic radicals, where the rings A and B are preferably not identical, and An⁻ represents an anion.

Possible nonionic radicals are, for example, $C_1$–$C_4$-alkyl, $C_1$–$C_4$-alkoxy, halogen, cyano, nitro, $C_1$–$C_4$-alkoxycarbonyl, $C_1$–$C_4$-alkylthio, $C_1$–$C_4$-alkanoylamino, benzoylamino, mono- or di-$C_1$–$C_4$-alkylamino.

Alkyl, alkoxy, aryl and heterocyclic radicals may, if desired, bear further radicals such as alkyl, halogen, nitro, cyano, CO—$NH_2$, alkoxy, trialkylsilyl, trialkylsiloxy or phenyl, the alkyl and alkoxy radicals can be straight-chain or branched, the alkyl radicals can be partially halogenated or perhalogenated, the alkyl and alkoxy radicals can be ethoxylated or propoxylated or silylated, adjacent alkyl and/or alkoxy radicals on aryl or heterocyclic radicals may together form a three- or four-membered bridge and the heterocyclic radicals can be benzo-fused and/or quaternized.

The radical of the formula II (II)

particularly preferably represents benzothiazol-2-yl, thiazol-2-yl, thiazolin-2-yl, benzoxazol-2-yl, oxazol-2-yl, oxazolin-2-yl, benzimidazol-2-yl, imidazol-2-yl, imidazolin-2-yl, pyrrolin-2-yl, 3-H-indol-2-yl, benz[c,d]indol-2-yl, 2- or 4-pyridyl or 2- or 4-quinolyl, where $X^1$ represents N, where the abovementioned rings may each be substituted by $C_1$–$C_6$-alkyl, $C_1$–$C_6$-alkoxy, fluorine, chlorine, bromine, iodine, cyano, nitro, $C_1$–$C_6$-alkoxycarbonyl, $C_1$–$C_6$-alkylthio, $C_1$–$C_6$-acylamino, $C_6$–$C_{10}$-aryl, $C_6$–$C_{10}$-aryloxy or $C_6$–$C_{10}$-arylcarbonylamino.

The radical of the formula III (III)

particularly preferably represents benzothiazol-2-ylidene, thiazol-2-ylidene, thiazolin-2-ylidene, isothiazol-3-ylidene, 1,3,4-thiadiazol-2-ylidene, 1,2,4-thiadiazol-5-ylidene, benzoxazol-2-ylidene, oxazol-2-ylidene, oxazolin-2-ylidene, 1,3,4-oxadiazol-2-ylidene, benzimidazol-2-ylidene, imidazol-2-ylidene, imidazolin-2-ylidene, pyrrolin-2-ylidene, 1,3,4-triazol-2-ylidene, 3H-indol-2-ylidene, benz[c,d]indol-2-ylidene, 2- or 4-pyridyl or 2- or 4-quinolyl, each of which bear the radical $R^2$, which is as defined above, on $X^3$ which represents N, where the abovementioned rings may each be substituted by $C_1$–$C_6$-alkyl, $C_1$–$C_6$-alkoxy, fluorine, chlorine, bromine, iodine, cyano, nitro, $C_1$–$C_6$-alkoxycarbonyl, $C_1$–$C_6$-alkylthio, $C_1$–$C_6$-acylamino, $C_6$–$C_{10}$-aryl, $C_6$–$C_{10}$-aryloxy, $C_6$–$C_{10}$-arylcarbonylamino, mono- or di-$C_1$–$C_6$-alkylamino, N—$C_1$–$C_6$-alkyl-N—$C_6$–$C_{10}$-arylamino, pyrrolidino, morpholino or piperazino.

In a particularly preferred embodiment, the cyanine dyes used are ones of the formula (I), in which the ring A and the ring B represent different heterocycles.

In a likewise particularly preferred embodiment, the cyanine dyes used are ones of the formula (I), in which Y represents N.

In a likewise particularly preferred embodiment, the cyanine dyes used are ones of the formula (I), in which Y represents C—CN.

In a likewise particularly preferred embodiment, the cyanine dyes used are ones of the formula (I), in which p represents 0 or 1.

Possible anions An⁻ include all monovalent anions or one equivalent of a polyvalent anion or one equivalent of an oligomeric or polymeric anion. Preference is given to colourless anions. Examples of suitable anions are chloride, bromide, iodide, tetrafluoroborate, perchlorate, hexafluorosilicate, hexafluorophosphate, methosulphate, ethosulphate, $C_1$–$C_{10}$-alkanesulphonate, $C_1$–$C_{10}$-perfluoroalkanesulphonate, unsubstituted or chloro-, hydroxy- or $C_1$–$C_4$-alkoxy-substituted $C_1$–$C_{10}$-alkanoate, unsubstituted or nitro-, cyano-, hydroxy-, $C_1$–$C_{25}$-alkyl-, perfluoro-$C_1$–$C_4$-alkyl-, $C_1$–$C_4$-alkoxycarbonyl- or chloro-substituted benzenesulphonate, or naphthalenesulphonate or biphenylsulphonate, unsubstituted or nitro-, cyano-, hydroxy-, $C_1$-$C_4$-alkyl-, $C_1$-$C_4$-alkoxy-, $C_1$-$C_4$-alkoxycarbonyl- or chloro-substituted benzenedisulphonate, naphthalenedisulphonate or biphenyldisulphonate, unsubstituted or nitro-, cyano-, $C_1$-$C_4$-alkyl, $C_1$-$C_4$-alkoxy-, $C_1$-$C_4$-alkoxycarbonyl-, benzoyl-, chlorobenzoyl- or toluyl-substituted benzoate, the anion of naphthalenedicarboxylic acid, (diphenyl ether)disulphonate, tetraphenylborate, cyanotriphenylborate, tetra-$C_1$-$C_{20}$-alkoxy-borate, tetraphenoxyborate, 7,8- or 7,9-dicarba-nido-undecaborate (1-) or (2-), which may, if desired, be substituted on the B- and/or C atoms by one or two $C_1$-$C_{12}$-alkyl or phenyl groups, dodecahydro-dicarbadodecaborate(2-) or B—$C_1$-$C_{12}$-alkyl-C-phenyl-dodecahydro-dicarbadodecaborate(1-), polystyrenesulphonate, poly(meth)acrylate, polyallylsulphonate.

Preference is given to bromide, iodide, tetrafluoroborate, perchlorate, hexafluorophosphate, methanesulphonate, trifluoromethanesulphonate, benzenesulphonate, toluenesulphonate, dodecylbenzenesulphonate, tetradecanesulphonate, polystyrenesulphonate.

In a very particularly preferred embodiment, the cyanine dyes used are ones of the formulae (IV) to (XII)

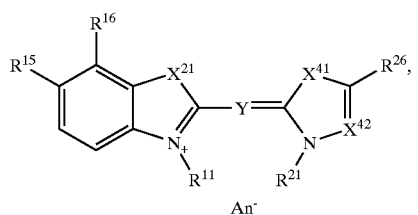
(IV)

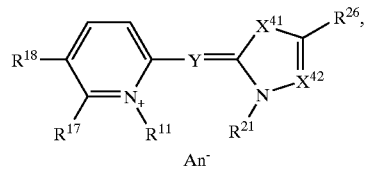
(V)

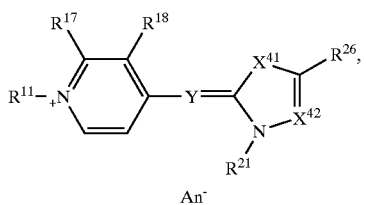
(VI)

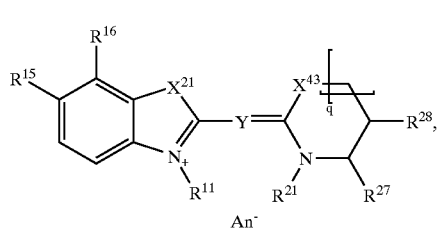
(VII)

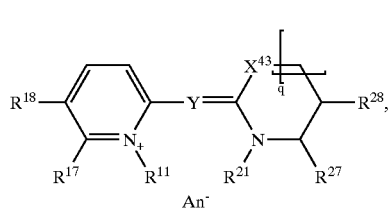
(VIII)

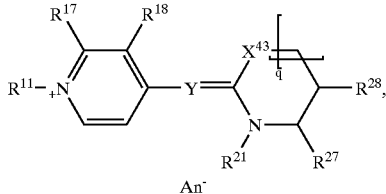
(IX)

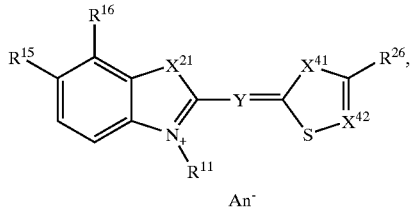
(X)

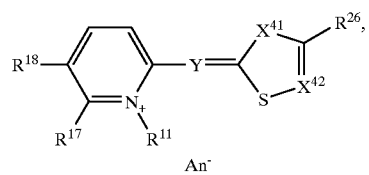
(XI)

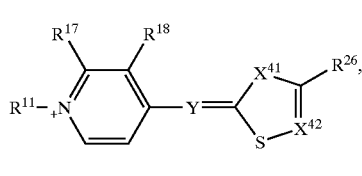
(XII)

where
$X^{21}$ represents O, S, N—$R^{12}$ or $CR^{13}R^{14}$,
$X^{41}$ and $X^{43}$ independently represent O, S, N—$R^{22}$ or $CR^{23}R^{24}$,
$X^{42}$ represents N or C—$R^{25}$,
$R^{11}$, $R^{12}$, $R^{21}$ and $R^{22}$ represent, independently of one another, methyl, ethyl, propyl, butyl, pentyl, hexyl, benzyl, phenethyl, cyclohexyl, chloroethyl, cyanomethyl, cyanoethyl, hydroxyethyl, 2-hydroxypropyl, methoxyethyl, ethoxyethyl or a radical of the formula

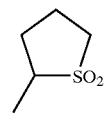

or
$R^{11}$ and $R^{21}$ represent a —$(CH_2)_2$— or —$(CH_2)_3$— bridge,
$R^{23}$ and $R^{24}$ represent hydrogen, methyl or ethyl or $CR^{23}R^{24}$ represents a bivalent radical of the formula

, where the two bonds go out from the ring atom marked with an asterisk (*), $R^{15}$ represents hydrogen, methyl, methoxy, chlorine, cyano, nitro, methoxycarbonly, methanesulphonyl or aminosulphonyl, $R^{16}$ represents hydrogen or $R^{15}$ and $R^{16}$ together represent a —CH=CH—CH=CH— bridge or $X^{21}$ and $R^{16}$ together represent *C=CH—CH=CH—, where two bonds go out from the atom marked with an asterisk (*), $R^{17}$ and $R^{18}$ represent hydrogen or together represent a —CH=CH—CH=CH— bridge, $R^{25}$ represents hydrogen, methyl, phenyl, chlorine, cyano, methoxycarbonyl, ethoxycarbonyl or methylthio, $R^{26}$ represents hydrogen, methyl, phenyl, methoxy, ethoxy, phenoxy, cyano, methoxycarbonyl, ethoxycarbonyl, methylthio, dimethylamino, diethylamino, dipropylamino, dibutylamino, pyrrolidino, piperidino, N-methylpiperazino or morpholino or $R^{25}$ and $R^{26}$ together represent a —(CH$_2$)$_3$—, —(CH$_2$)$_4$—, —S—(CH$_2$)$_2$—S— or —CH=CH—CH=CH— bridge which may be substituted by methyl, methoxy, chloro, cyano, nitro, methoxycarbonyl, methanesulphonyl or aminosulphonyl, $R^{27}$ and $R^{28}$ represent, independently of one another, hydrogen or methyl or together form a —(CH$_2$)$_3$— or —(CH$_2$)$_4$— bridge, q represents 0 or 1, Y represents CH, C—CN or N and An⁻ represents tetrafluoroborate, perchlorate, hexafluorophosphate, iodide, thiocyanate, cyanate, hydroxyacetate, methoxyacetate, lactate, citrate, methanesulphonate nesulphonate, ethanesulphonate, trifluoromethanesulphonate, benzenesulphonate, toluenesulphonate, butylbenzenesulphonate, chlorobenzenesulphonate, dodecylbenzenesulphonate, naphthalenesulphonate or one equivalent of polystyrenesulphonate, where in the case of the cyanine dyes of the formula (IV), $X^{21}$ and $X^{41}$ must not be identical when $X^{42}$ represents C—$R^{25}$ and $R^{25}$ and $R^{26}$ together represent a —CH=CH—CH=CH— bridge.

In the formulae (IV) to (XII), it is especially preferred that $X^{21}$ represents O or S, $X^{41}$ represents S or C(CH$_3$)$_2$, $X^{42}$ represents N or C—$R^{25}$, $R^{25}$ represents hydrogen or together with $R^{26}$ represents a —CH=CH—CH=CH— bridge, $X^{43}$ represents S or CH$_2$, $R^{27}$ and $R^{28}$ represent hydrogen, q represents 0 and Y represents N or CH, where the other radicals are as defined above.

In a likewise very particularly preferred embodiment, the cyanine dyes used are ones of the formulae (XIII) to (XXV)

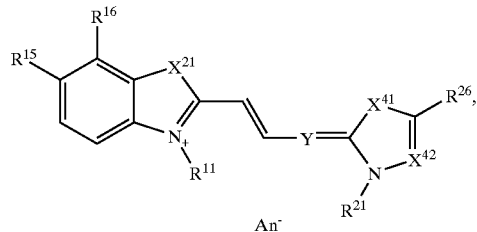

(XIII)

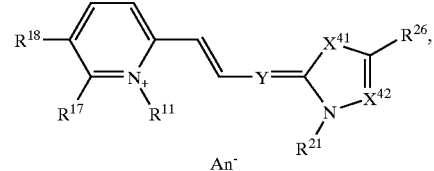

(XIV)

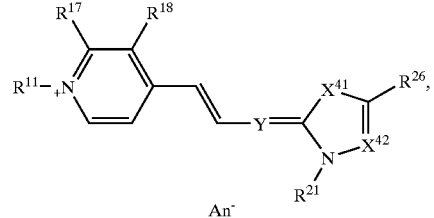

(XV)

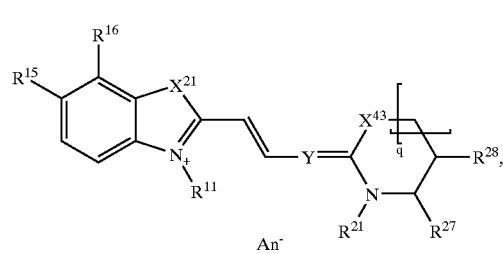

(XVI)

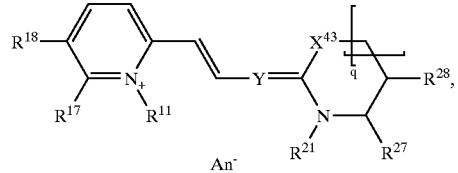

(XVII)

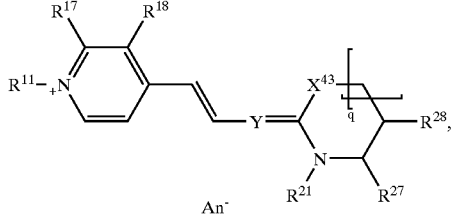

(XVIII)

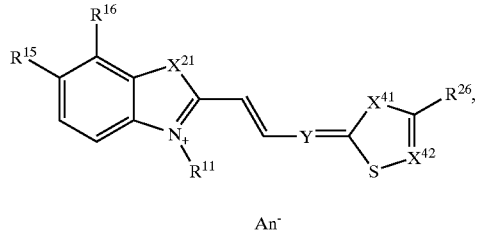

(XIX)

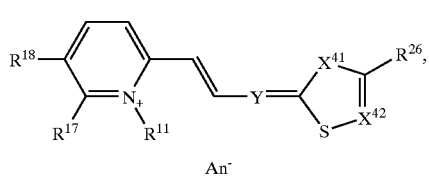 (XX)

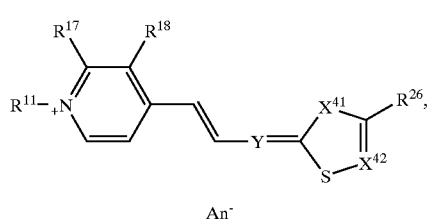 (XXI)

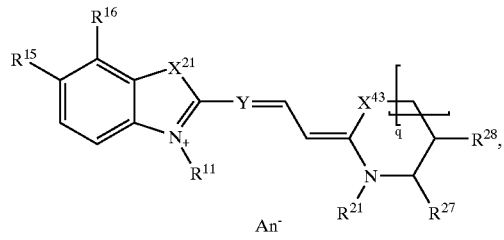 (XXII)

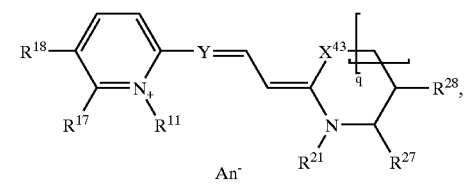 (XXIII)

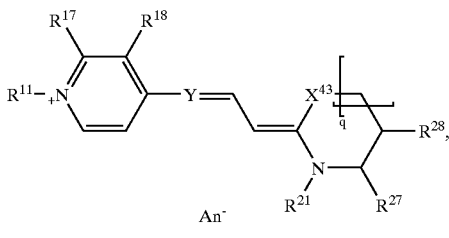 (XXIV)

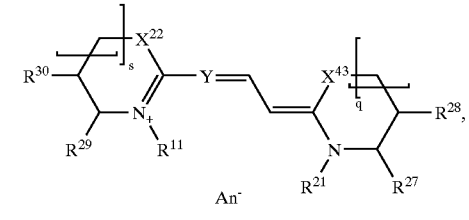 (XXV)

where $X^{21}$ represents O, S, N—$R^{12}$ or $CR^{13}R^{14}$, $X^{22}$, $X^{41}$ and $X^{43}$ independently represent O, S, N—$R^{22}$ or $CR^{23}R^{24}$, $X^{42}$ represents N or C—$R^{25}$, $R^{11}$, $R^{12}$, $R^{21}$ and $R^{22}$ represent, independently of one another, methyl, ethyl, propyl, butyl, pentyl, hexyl, benzyl, phenethyl, cyclohexyl, chloroethyl, cyanomethyl, cyanoethyl, hydroxyethyl, 2-hydroxypropyl, methoxyethyl, ethoxyethyl or a radical of the formula

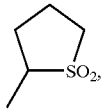

$R^{23}$ and $R^{24}$ represent hydrogen, methyl or ethyl or $CR^{23}R^{24}$ represents a bivalent radical of the formula

where the two bonds go out from the ring atom marked with an asterisk (*), $R^{15}$ represents hydrogen, methyl, methoxy, chlorine, cyano, nitro, methoxycarbonly, methanesulphonyl or aminosulphonyl, $R^{16}$ represents hydrogen or $R^{15}$ and $R^{16}$ together represent a —CH=CH—CH=CH— bridge or $X^{21}$ and $R^{16}$ together represent *C=CH—CH=CH—, where two bonds go out from the atom marked with an asterisk (*), $R^{17}$ and $R^{18}$ represent hydrogen or together represent a —CH=CH—CH=CH— bridge, $R^{25}$ represents hydrogen, methyl, phenyl, chlorine, cyano, methoxycarbonyl, ethoxycarbonyl or methylthio, $R^{26}$ represents hydrogen, methyl, phenyl, methoxy, ethoxy, phenoxy, cyano, methoxycarbonyl, ethoxycarbonyl, methylthio, dimethylamino, diethylamino, dipropylamino, dibutylamino, pyrrolidino, piperidino, N-methylpiperazino or morpholino or $R^{25}$ and $R^{26}$ together represent a —$(CH_2)_3$—, —$(CH_2)_4$—, —S—$(CH_2)_2$—S— or —CH=CH—CH=CH— bridge which may be substituted by methyl, methoxy, chlorine, cyano, nitro, methoxycarbonyl, methanesulphonyl or aminosulphonyl, $R^{27}$ to $R^{30}$ represent, independently of one another, hydrogen or methyl or $R^{27}$ and $R^{28}$ or $R^{29}$ and $R^{30}$ together represent a —$(CH_2)_3$— or —$(CH_2)_4$— bridge, q and s represent, independently of one another, 0 or 1, Y represents CH, C—CN or N and $An^-$ represents tetrafluoroborate, perchlorate, hexafluorophosphate, iodide, thiocyanate, cyanate, hydroxyacetate, methoxyacetate, lactate, citrate, methanesulphonate, ethanesulphonate, trifluoromethanesulphonate, benzenesulphonate, toluenesulphonate, butylbenzenesulphonate, chlorobenzenesulphonate, dodecylbenzenesulphonate, naphthalenesulphonate or one equivalent of polystyrenesulphonate, where in the case of the cyanine dyes of the formula (XIII), $X^{21}$ and $X^{41}$ are preferably not identical when $X^{42}$ represents C—$R^{25}$, $R^{25}$ and $R^{26}$ together represent a —CH=CH—CH=CH— bridge and Y represents CH, and in the case of the cyanine dyes of the formula (XXV), $X^{22}$ and $X^{43}$ must not be identical when q and s are identical and Y represents CH.

In the formulae (XIII) to (XXV), it is especially preferred that $X^{21}$ represents O, S or $C(CH_3)_2$, $X^{41}$ represents S or $C(CH_3)_2$, $X^{42}$ represents N or C—$R^{25}$, $R^{25}$ represents hydrogen or together with $R^{26}$ represents a —CH=CH—CH=CH— bridge, $X^{22}$ and $X^{43}$ represent, independently of one another, S or $CH_2$, $R^{27}$ to $R^{30}$ represent hydrogen, q and s represent 0 and Y represents N, CH or C—CN, where the other radicals are as defined above, where in the case of the cyanine dyes of the formula (XIII), $X^{21}$ and $X^{41}$ are preferably not identical when $X^{42}$ represents C—$R^{25}$, $R^{25}$ and $R^{26}$ together represent a —CH=CH—CH=CH— bridge and Y represents CH, and in the case of the cyanine dyes of the formula (XXV), $X^{22}$ and $X^{43}$ must not be identical when Y represents CH.

In a likewise very particularly preferred embodiment, the cyanine dyes used are ones of the formulae (XXVI) to (XXXVII)

(XXVI)
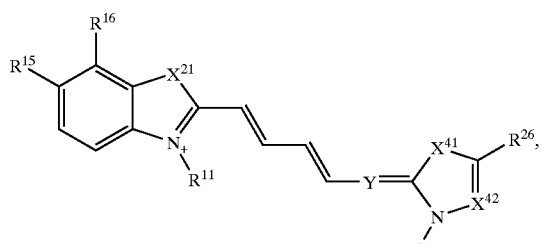

(XXVII)
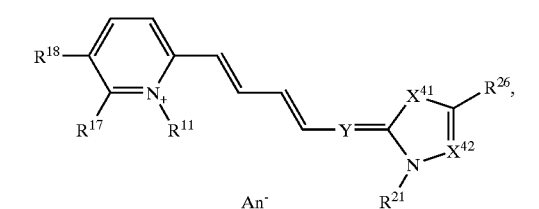

(XXVIII)
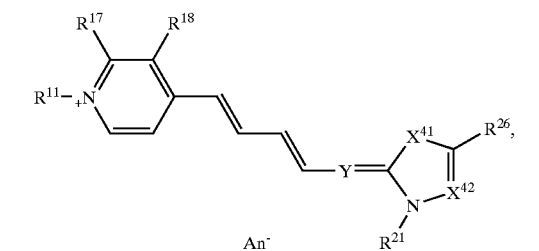

(XXIX)
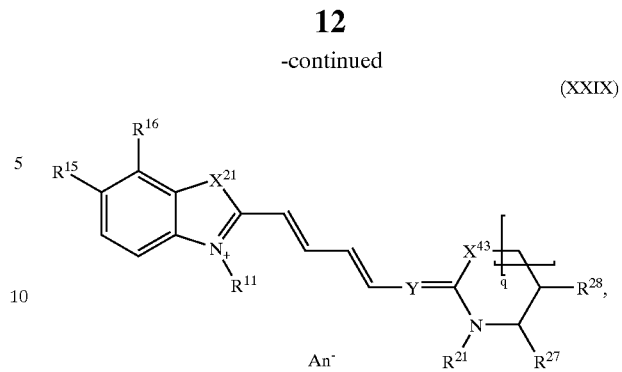

(XXX)
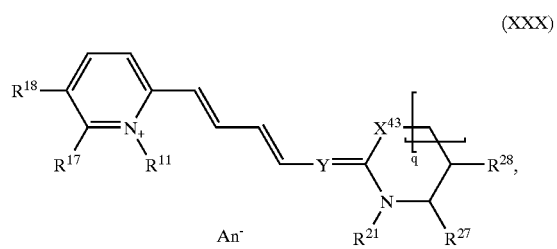

(XXXI)
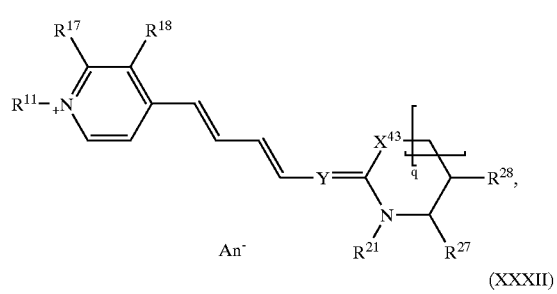

(XXXII)
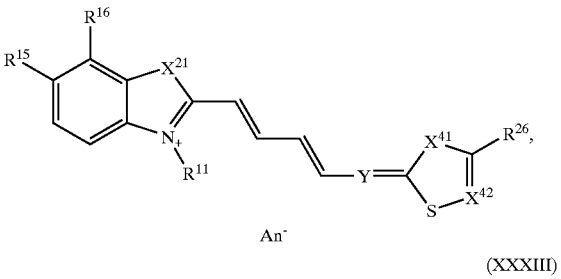

(XXXIII)
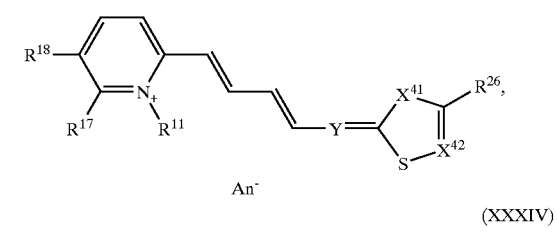

(XXXIV)
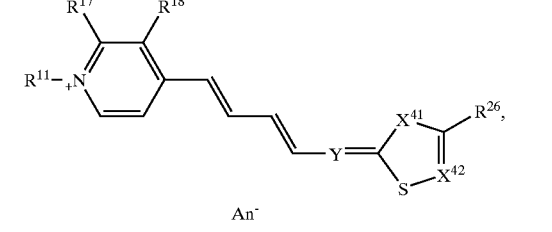

-continued

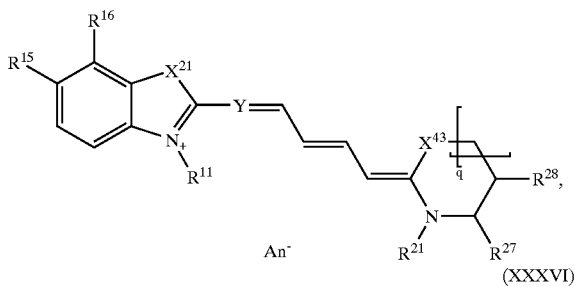

(XXXV)

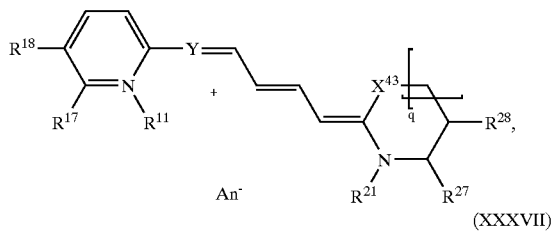

(XXXVI)

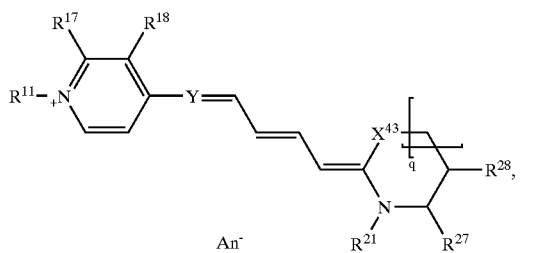

(XXXVII)

where $X^2$ represents O, S, N—$R^{12}$ or $CR^{13}R^{14}$, $X^{41}$ and $X^{43}$ independently represent O, S, N—$R^{22}$ or $CR^{23}R^{24}$, $X^{42}$ represents N or C—$R^{25}$, $R^{11}$, $R^{12}$, $R^{21}$ and $R^{22}$ represent, independently of one another, methyl, ethyl, propyl, butyl, pentyl, hexyl, benzyl, phenethyl, cyclohexyl, chloroethyl, cyanomethyl, cyanoethyl, hydroxyethyl, 2-hydroxypropyl, methoxyethyl, ethoxyethyl or a radical of the formula

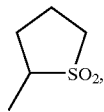

$R^{23}$ and $R^{24}$ represent hydrogen, methyl or ethyl or $CR^{23}R^{24}$ represents a bivalent radical of the formula

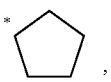

where the two bonds go out from the ring atom marked with an asterisk (*), $R^{15}$ represents hydrogen, methyl, methoxy, chlorine, cyano, nitro, methoxycarbonyl, methanesulphonyl or aminosulphonyl, $R^{16}$ represents hydrogen or $R^{15}$ and $R^{16}$ together represent a —CH=CH—CH=CH— bridge or $X^{21}$ and $R^{16}$ together represent *C=CH—CH=CH—, where two bonds go out from the atom marked with an asterisk (*), $R^{17}$ and $R^{18}$ represent hydrogen or together represent a —CH=CH—CH=CH— bridge, $R^{25}$ represents hydrogen, methyl, phenyl, chlorine, cyano, methoxycarbonyl, ethoxycarbonyl or methylthio, $R^{26}$ represents hydrogen, methyl, phenyl, methoxy, ethoxy, phenoxy, cyano, methoxycarbonyl, ethoxycarbonyl, methylthio, dimethylamino, diethylamino, dipropylamino, dibutylamino, pyrrolidino, piperidino, N-methylpiperazino or morpholino or $R^{25}$ and $R^{26}$ together represent a —(CH$_2$)$_3$—, —(CH$_2$)$_4$—, —S—(CH$_2$)$_2$—S— or —CH=CH—CH=CH— bridge which may be substituted by methyl, methoxy, chlorine, cyano, nitro, methoxycarbonyl, methanesulphonyl or aminosulphonyl, $R^{27}$ and $R^{28}$ represent, independently of one another, hydrogen or methyl or together represent a —(CH$_2$)$_3$— or —(CH$_2$)$_4$— bridge, q represents 0 or 1, Y represents CH, C—CN or N and An$^-$ represents tetrafluoroborate, perchlorate, hexafluorophosphate, iodide, thiocyanate, cyanate, hydroxyacetate, methoxyacetate, lactate, citrate, methanesulphonate, ethanesulphonate, trifluoromethanesulphonate, benzenesulphonate, toluenesulphonate, butylbenzebesulphonate, chlorobenzenesulphonate, dodecylbenzenesulphonate, naphthalenesulphonate or one equivalent of polystyrenesulphonate, where in the case of the cyanine dyes of the formula (XXVI), $X^{21}$ and $X^{41}$ are preferably not identical when $X^{42}$ represents C—$R^{25}$, $R^{25}$ and $R^{26}$ together represent a —CH=CH—CH=CH— bridge and Y represents CH.

Exceptional preference is given to cyanine dyes of the formulae (XXVI) to (XXVIII) and (XXXII) to (XXXIV) in which $X^{21}$ represents O, S or C(CH$_3$)$_2$, $X^{41}$ represents S or C(CH$_3$)$_2$, $X^{42}$ represents N or C—$R^{25}$, $R^{25}$ represents hydrogen or together with $R^{26}$ represents a —CH=CH—CH=CH— bridge, $X^{43}$ represents S or CH$_2$, $R^{27}$ and $R^{28}$ represent hydrogen, q represents 0 and Y represents N, CH or C—CN, where the other radicals are as defined above, where in the case of the cyanine dyes of the formula (XXVI), $X^{21}$ and $X^{41}$ are preferably not identical when $X^{42}$ represents C—$R^{25}$, $R^{25}$ and $R^{26}$ together represent a —CH=CH—CH=CH— bridge and Y represents CH.

In the case of a write-once optical data carrier according to the invention which is written on and read by means of the light of a blue laser, preference is given to cyanine dyes whose absorption maximum $\lambda_{max1}$ is in the range from 340 to 410 nm, where the wavelength $\lambda_{1/2}$ at which the absorbance in the long wavelength flank of the absorption maximum at the wavelength $\lambda_{max1}$ is half of the absorbance value at $\lambda_{max1}$ and the wavelength $\lambda_{1/10}$ at which the absorbance in the long wavelength flank of the absorption maximum at the wavelength $\lambda_{max1}$ is one tenth of the absorbance value at $\lambda_{max1}$ are preferably not more than 50 nm apart. Such a cyanine dye preferably has no longer-wavelength maximum $\lambda_{max2}$ up to a wavelength of 500 nm, particularly preferably 550 nm, very particularly preferably 600 nm.

Preference is given to cyanine dyes having an absorption maximum $\lambda_{max1}$ of from 345 to 400 nm.

Particular preference is given to cyanine dyes having an absorption maximum $\lambda_{max1}$ of from 350 to 380 nm.

Very particular preference is given to cyanine dyes having an absorption maximum $\lambda_{max1}$ of from 360 to 370 nm.

In the case of these dyes, $\lambda_{1/2}$ and $\lambda_{1/10}$, as defined above, are preferably not more than 40 nm apart, particularly preferably not more than 30 nm apart, very particularly preferably not more than 10 nm apart.

Dyes which are suitable in this respect are ones of the formulae (IV) to (VI) and (X) to (XII), in which Y is N, and ones of the formulae (VII) to (IX) in which Y is CH.

In the case of a write-once optical data carrier according to the invention which is written on and read by means of the light of a blue laser, preference is also given to cyanine dyes whose absorption maximum $\lambda_{max2}$ is in the range from 420 to 550 nm, where the wavelength $\lambda_{1/2}$ at which the absorbance in the short wavelength flank of the absorption maximum at the wavelength $\lambda_{max2}$ is half of the absorbance value at $\lambda_{max2}$ and the wavelength $\lambda_{1/10}$ at which the absorbance in the short wavelength flank of the absorption maximum at the wavelength $\lambda_{max2}$ is one tenth of the absorbance value at $\lambda_{max2}$ are preferably not more than 50 nm apart. Such a cyanine dye preferably has no shorter-wavelength maximum $\lambda_{max1}$ down to a wavelength of 350 nm, particularly preferably down to 320 nm, very particularly preferably down to 290 nm.

Preference is given to cyanine dyes having an absorption maximum $\lambda_{max2}$ of from 410 to 530 nm.

Particular preference is given to cyanine dyes having an absorption maximum $\lambda_{max2}$ of from 420 to 510 nm.

Very particular preference is given to cyanine dyes having an absorption maximum $\lambda_{max2}$ of from 430 to 500 nm.

In these cyanine dyes, $\lambda_{1/2}$ and $\lambda_{1/10}$, as defined above, are preferably not more than 40 nm apart, particularly preferably not more than 30 nm apart, very particularly preferably not more than 20 nm apart.

Dyes which are suitable in this respect are ones of the formula (IV) to (VI) and (X) to (XII), in which Y represents CH, and ones of the formulae (XIII) to (XXIV).

In the case of a write-once optical data carrier according to the invention which is written on and read by means of the light of a red laser, preference is given to cyanine dyes whose absorption maximum $\lambda_{max2}$ is in the range from 500 to 650 nm, where the wavelength $\lambda_{1/2}$ at which the absorbance in the long wavelength flank of the absorption maximum at the wavelength $\lambda_{max2}$ is half of the absorbance value at $\lambda_{max2}$ and the wavelength $\lambda_{1/10}$ at which the absorbance in the long wavelength flank of the absorption maximum at the wavelength $\lambda_{max2}$ is one tenth of the absorbance value at $\lambda_{max2}$ are preferably not more than 50 nm apart. Such a cyanine dye preferably has no longer-wavelength maximum $\lambda_{max3}$ up to a wavelength of 750 nm, particularly preferably up to 800 nm, very particularly preferably up to 850 nm.

Preference is given to cyanine dyes having an absorption maximum $\lambda_{max2}$ of from 530 to 630 nm.

Particular preference is given to cyanine dyes having an absorption maximum $\lambda_{max2}$ of from 550 to 620 nm.

Very particular preference is given to cyanine dyes having an absorption maximum $\lambda_{max2}$ of from 580 to 610 nm.

In these cyanine dyes, $\lambda_{1/2}$ and $\lambda_{1/10}$, as defined above, are preferably not more than 40 nm apart, particularly preferably not more than 30 nm apart, very particularly preferably not more than 20 nm apart.

Dyes which are suitable in this respect are ones of the formulae (XIII) to (XV) and (XIX) to (XXI).

In the case of a write-once optical data carrier according to the invention which is written on and read by means of the light of a infrared laser, preference is given to cyanine dyes whose absorption maximum $\lambda_{max3}$ is in the range from 650 to 810 nm, where the wavelength $\lambda_{1/2}$ at which the absorbance in the long wavelength flank of the absorption maximum at the wavelength $\lambda_{max3}$ is half of the absorbance value at $\lambda_{max3}$ and the wavelength $\lambda_{1/10}$ at which the absorbance in the long wavelength flank of the absorption maximum at the wavelength $\lambda_{max3}$ is one tenth of the absorbance value at $\lambda_{max3}$ are preferably not more than 50 nm apart.

Preference is given to cyanine dyes having an absorption maximum $\lambda_{max3}$ of from 660 to 790 nm.

Particular preference is given to cyanine dyes having an absorption maximum $\lambda_{max3}$ of from 670 to 760 nm.

Very particular preference is given to cyanine dyes having an absorption maximum $\lambda_{max3}$ of from 680 to 740 nm.

In these cyanine dyes, $\lambda_{1/2}$ and $\lambda_{1/10}$, as defined above, are preferably not more than 40 nm apart, particularly preferably not more than 30 nm apart, very particularly preferably not more than 20 nm apart.

Dyes which are suitable in this respect are ones of the formulae (XXV) to (XXVII) and (XXXI) to (XXXIII).

The cyanine dyes have a molar extinction coefficient $\epsilon$ of >40 000 l/mol cm, preferably >60 000 l/mol cm, particularly preferably >80 000 l/mol cm, very particularly preferably >100 000/mol cm, at the absorption maximum $\lambda_{max2}$.

The absorption spectra are measured, for example, in solution.

Suitable cyanine dyes having the required spectral properties are, in particular, those in which the dipole moment change $\Delta\mu=|\mu_g-\mu_{ag}|$, i.e. the positive difference between the dipole moments in the ground state and in the first excited state, is very small, preferably <5 D, particularly preferably <2 D. A method of determining such a dipole moment change $\Delta\mu$ is described, for example, in F. Würthner et al., Angew. Chem. 1997, 109, 2933, and in the literature cited therein. A low solvent-induced wavelength shift (methanol/methylene chloride) is likewise a suitable selection criterion. Preference is given to cyanine dyes whose solvent-induced wavelength shift $\Delta\lambda=|\lambda_{methylene\ chloride}-\lambda_{methanol}|$, i.e. the positive difference between the absorption wavelengths in the solvents methylene chloride and methanol, is <25 nm, particularly preferably <15 nm, very particularly preferably <5 nm.

Some cyanine dyes of the formula (I) are known, e.g. from DE-C 883 025, DE-A 1 070 316, DE-A 1 170 569, J. Chem. Soc. 1951, 1087, Ann. Soc. Chim. Pol. 1963, 225.

The invention further provides cyanine dyes of the formula

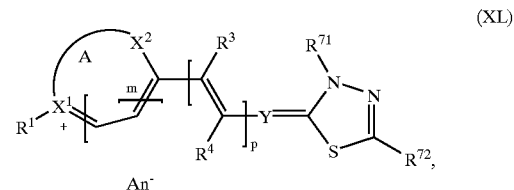

(XL)

where
  $R^{71}$ represents $C_1$–$C_{16}$-alkyl, $C_3$–$C_6$-alkenyl, $C_5$–$C_7$-cycloalkyl or $C_7$–$C_{16}$-aralkyl, $R^{72}$ represents $C_1$–$C_{16}$-alkoxy, $C_1$–$C_{16}$-alkylthio, di-$C_1$–$C_{16}$-alkylamino, N—$C_1$–$C_{16}$-alkyl-N—$C_6$–$C_{10}$-arylamino, pyrrolidino, piperidino, piperazino or morpholino, Y represents N and the other radicals have the meanings given above for the formula (I).

Preference is given to cyanine dyes of the formula (XL) in which $R^1$ and $R^{71}$ represent, independently of one another, methyl, ethyl, propyl, butyl or benzyl, $R^{72}$ represents dimethylamino, diethylamino, dipropylamino, dibutylamino, pyrrolidino, piperidino oder morpholino, Y represents N, p represents 0 or 1, $R^3$ and $R^4$ represent hydrogen and the ring A represents benzothiazol-2-yl, thiazol-2-yl, thiazolin-2-yl, benzoxazol-2-yl, pyrrolin-2-yl or 3,3-dimethyl-3H-indol-2-yl, where benzothiazol-2-yl, thiazol-2-yl, benzoxazol-2-yl and 3,3-dimethyl-3H-indol-2-yl may be substituted by methyl, methoxy, chlorine, cyano, nitro or methoxycarbonyl, and $An^-$ represents an anion.

Particular preference is given to p being 1 and the ring A representing 3,3-dimethyl-3H-indol-2-yl, 5-methyl-3,3-dimethyl-3H-indol-2-yl, 5-methoxy-3,3-dimethyl-3H-indol-2-yl, 5-nitro-3,3-dimethyl-3H-indol-2-yl, 5-chloro-3,3-dimethyl-3H-indol-2-yl or 5-methoxycarbonyl-3,3-dimethyl-3H-indol-2-yl, very particularly preferably 3,3-dimethyl-3H-indol-2-yl.

The invention further provides cyanine dyes of the formula (XLI)

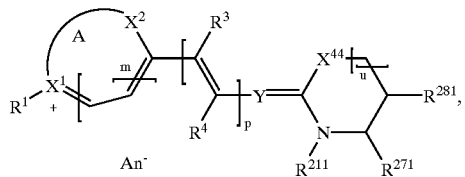

where $R^{211}$ represents $C_1$–$C_{16}$-alkyl, $C_3$–$C_6$-alkenyl, $C_5$–$C_7$-cycloalkyl or $C_7$–$C_{16}$-aralkyl, $X^{44}$ represents S, O or CH, $R^{271}$ and $R^{281}$ represent, independently of one another, hydrogen or $C_1$–$C_3$-alkyl or together represent a —(CH$_2$)$_3$— or —(CH$_2$)$_4$— bridge, u represents 0 or 1, Y represents CH and the other radicals have the meanings given above for the formula (I).

Preference is given to cyanine dyes of the formula (XLI) in which $R^1$ and $R^{211}$ represent, independently of one another, methyl, ethyl, propyl, butyl or benzyl, $X^{44}$ represents S or CH, $R^{271}$ and $R^{281}$ represent hydrogen, u represents 0 or 1, p represents 0 or 1, $R^3$ and $R^4$ represent hydrogen and the ring A represents benzothiazol-2-yl, thiazol-2-yl, thiazolin-2-yl, benzoxazol-2-yl, pyrrolin-2-yl or 3,3-dimethyl-3H-indol-2-yl, where benzothiazol-2-yl, thiazol-2-yl, benzoxazol-2-yl and 3,3-dimethyl-3H-indol-2-yl may be substituted by methyl, methoxy, chlorine, cyano, nitro or methoxycarbonyl, and $An^-$ represents an anion.

Particular preference is given to p being 1 and the ring A representing 3,3-dimethyl-3H-indol-2-yl, 5-methyl-3,3-dimethyl-3H-indol-2-yl, 5-methoxy-3,3-dimethyl-3H-indol-2-yl, 5-nitro-3,3-dimethyl-3H-indol-2-yl, 5-chloro-3,3-dimethyl-3H-indol-2-yl or 5-methoxycarbonyl-3,3-dimethyl-3H-indol-2-yl, very particularly preferably 3,3-dimethyl-3H-indol-2-yl.

Preference is likewise given to p being 0 and the ring A representing benzothiazol-2-yl, 5-methoxy-benzothiazol-2-yl, 5-chloro-benzothiazol-2-yl, 5-cyano-benzothiazol-2-yl, 3,3-dimethyl-3H-indol-2-yl, 5-methyl-3,3-dimethyl-3H-indol-2-yl, 5-methoxy-3,3-dimethyl-3H-indol-2-yl, 5-nitro-3,3-dimethyl-3H-indol-2-yl, 5-chloro-3,3-dimethyl-3H-indol-2-yl or 5-methoxycarbonyl-3,3-dimethyl-3H-indol-2-yl, very particularly preferably benzothiazol-2-yl or 3,3-dimethyl-3H-indol-2-yl.

The cyanine dyes can be prepared by methods known per se.

The light-absorbent compounds described guarantee a sufficiently high reflectivity (>10%) of the optical data carrier in the unwritten state and a sufficiently high absorption for thermal degradation of the information layer on point-wise illumination with focused light if the wavelength of the light is in the range from 360 to 460 nm and from 600 to 680 nm. The contrast between written and unwritten points on the data carrier is achieved by the reflectivity change of the amplitude and also the phase of the incident light due to the changed optical properties of the information layer after the thermal degradation.

The cyanine dyes are preferably applied to the optical data carrier by spin coating or vacuum vapour deposition. The cyanine dyes can be mixed with one another or with other dyes having similar spectral properties. In particular, dyes containing different anions can also be mixed. The information layer can comprise not only the cyanine dyes but also additives such as binders, wetting agents, stabilizers, diluents and sensitizers and also further constituents.

It is likewise possible to use mixtures with other, preferably cationic dyes. The other dyes used for the mixture are preferably ones whose $\lambda_{max}$ differs by not more than 30 nm, preferably not more than 20 nm, very particularly preferably not more than 10 nm, from the $\lambda_{max2}$ or $\lambda_{max3}$ of the dye of the formula (I). Examples which may be mentioned are dyes of the classes of cyanines, streptocyanines, hemicyanines, diazahemicyanines, nullmethines, enamine dyes, hydrazone dyes, di- or tri(het)arylmethane dyes, xanthene dyes, azine dyes (phenazines, oxazines, thiazines) or, for example, from the classes of azo dyes, anthraquinone dyes, neutrocyanines, porphyrins or phthalocyanines. Such dyes are known, for example, from H. Berneth, Cationic Dyes in Ullmann's Encyclopedia of Industrial Chemistry, VCH, 6$^{th}$ edition.

Apart from the information layer, further layers such as metal layers, dielectric layers, barrier layers and protective layers may be present in the optical data carrier. Metals and dielectric and/or barrier layers serve, inter alia, to adjust the reflectivity and the heat absorption/retention. Metals can be, depending on the laser wavelength, gold, silver, aluminium, etc. Examples of dielectric layers are silicon dioxide and silicon nitride. Barrier layers are dielectric or metal layers.

Protective layers are, for example, photocurable surface coatings, (pressure-sensitive) adhesive layers and protective films.

Pressure-sensitive adhesive layers consist mainly of acrylic adhesives. Nitto Denko DA-8320 or DA-8310, disclosed in the patent JP-A 11-2731471, can, for example, be used for this purpose.

The optical data carrier has, for example, the following layer structure (cf. FIG. 1): a transparent substrate (1), if desired a protective layer (2), an information layer (3), if desired a protective layer (4), if desired an adhesive layer (5), a covering layer (6).

The structure of the optical data carrier preferably:

comprises a preferably transparent substrate (1) to whose surface at least one light-writeable information layer (3) which can be written on by means of light, preferably laser light, if desired a protective layer (4), if desired an adhesive layer (5) and a transparent covering layer (6) have been applied.

comprises a preferably transparent substrate (1) to whose surface a protective layer (2), at least one information layer (3) which can be written on by means of light, preferably laser light, if desired an adhesive layer (5) and a transparent covering layer (6) have been applied.

comprises a preferably transparent substrate (1) to whose surface a protective layer (2) if desired, at least one information layer (3) which can be written on by means of light, preferably laser light, if desired a protective layer (4), if desired an adhesive layer (5) and a transparent covering layer (6) have been applied.

comprises a preferably transparent substrate (1) to whose surface at least one information layer (3) which can be written on by means of light, preferably laser light, if desired an adhesive layer (5) and a transparent covering layer (6) have been applied.

Figure 2:
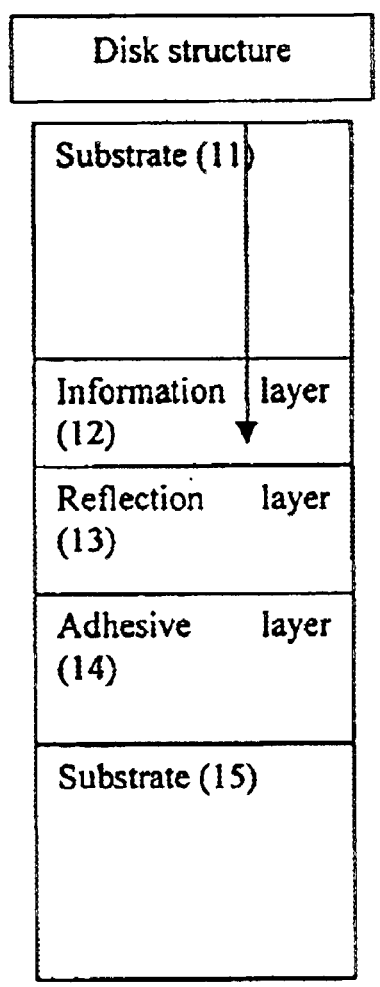
FIG. 2 illustrates an alternate embodiment of an optical data carrier with a layer structure of a transparent substrate, an information layer, if desired a reflection layer, if desired an adhesive layer, a further transparent substrate.

Alternatively, the optical data carrier has, for example, the following layer structure (cf. FIG. 2): a preferably transparent substrate (11), an information layer (12), if desired a reflection layer (13), if desired an adhesive layer (14), a further preferably transparent substrate (15).

The invention further provides optical data supports according to the invention which have been written on by means of blue or red light, in particular laser light.

The following examples illustrate the subject-matter of the invention.

EXAMPLES

Example 1

8.1 g of 2-amino-3-methyl-5-diisopropylamino-1,3,4-thiadiazolium methosulphate, prepared from 2-amino-5-diisopropylamino-1,3,4-thiadiazole and dimethyl sulphate, and 5 g of 1,3,3-trimethyl-2-methylene-3H-indol-ω-aldehyde were boiled in a mixture of 25 ml of toluene and 2,3 g of methanesulphonic acid for 12 hours using a water separator. After cooling, 50 ml of hexane were added and the oil which separated out was separated off. This was taken up in 200 ml of water. The aqueous phase was extracted three times with 200 ml each time of chloroform. The chloroform phase was evaporated on a rotary evaporator. This gave 2.3 g (19% of theory) of a red powder of the formula

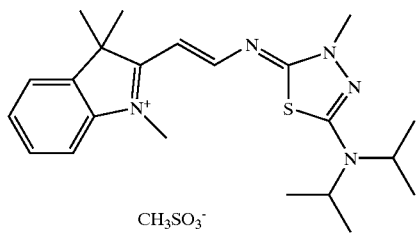

m.p.=115° C.
$\lambda_{max}$(methanol)=544 nm
$\epsilon$=96235 l/mol cm
$\lambda_{1/2}-\lambda_{1/10}$(short wavelength flank)=36 nm
$\lambda_{1/2}-\lambda_{1/10}$(long wavelength flank)=13 nm
Solubility: >2% in TFP (2,2,3,3-tetrafluoropropanol)
Glass-like film Example 2

3.1 g of 1-methyl-2-methylthio-benzothiazolium methosulphate, prepared from 2-methylthiobenzothiazole and dimethyl sulphate, and 2.6 g of 1-ethyl-2-methylthiazolinium iodide, prepared from 2-methylthiazoline and ethyl iodide, were boiled in 50 ml of pyridine for 3 hours. After cooling, the solid was filtered off with suction, washed with 5 ml of pyridine and dried. This gave 1.1 g (27% of theory) of a colourless powder of the formula

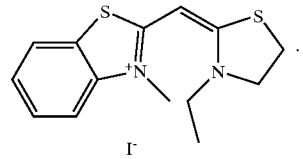

m.p.=250–254° C.
$\lambda_{max}$(methanol)=384 nm
$\epsilon$=54621 l/mol cm
$\lambda_{1/2}-\lambda_{1/10}$(long wavelength flank)=10 nm
Solubility: 5% in TFP (2,2,3,3-tetrafluoropropanol)

0.4 g of the above product were stirred under reflux in 15 ml of methanol together with 0.1 g of lithium perchlorate for 1 hour. After cooling, the solid was filtered off with suction, washed with 3 ml of methanol and dried. This gave 0.3 g (80% of theory) of a colourless powder of the formula

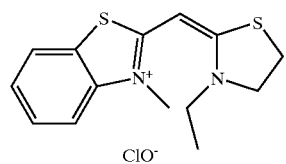

m.p.=220–225° C.
$\lambda_{max}$(methanol)=384 nm
$\epsilon$=56117 l/mol cm
$\lambda_{1/2}-\lambda_{1/10}$(long wavelength flank)=10 nm
Solubility: 5% in TFP (2,2,3,3-tetrafluoropropanol)
Glass-like film Cyanine dyes which are likewise suitable are shown in the following table:

| Example | $R^1-\underset{+}{X^1}\underset{A}{\overset{X^2}{\diagdown}}$ | $\overset{R^3}{\underset{R^4}{\diagup}}=\underset{p}{(Y=)}$ | $\underset{X^4}{\overset{X^3}{\diagdown}}\underset{B}{\overset{}{\diagup}}\underset{n}{(X^3=)}R^2$ | An⁻ | $\lambda_{max}/nm^{1)}$ | $\epsilon/l/mol\,cm$ | $\lambda_{1/2}\text{-}\lambda_{1/10}/nm\,\Delta\lambda^{2)}/nm$ |
|---|---|---|---|---|---|---|---|
| 3 | 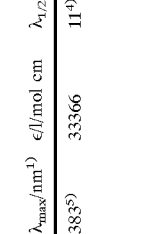 | —N= |  | ClO₄⁻ | 383[5] | 33366 | 11[4] |
| 4 |  | —N= |  | BF₄⁻ | 366[5] | 36195 | 9[4] |
| 5 |  | —CH= |  | ClO₄⁻ | 436[5] | 48882 | 27[3] |
| 6 |  | —CH= |  | ClO₄⁻ | 463, 488[5] | 47439 | 19[4] |
| 7 | | —N= | | BF₄⁻ | 400 | 75504 | 9[4] |

-continued

| Example | A ring (R¹—X¹⁺, X², m) | R³, R⁴, Y, p | B ring (X³, X⁴, R², n) | An⁻ | $\lambda_{max}$/nm[1] | $\epsilon$/l/mol cm | $\lambda_{1/2}$-$\lambda_{1/10}$/nm $\Delta\lambda^{2)}$/nm[4] |
|---|---|---|---|---|---|---|---|
| 8 | 2-methyl-3-ethyl-benzothiazolium | —CH= | 2-methylene-3-ethyl-thiazolidine | I⁻ | 384 | 48321 | 11 [4] |
| 9 | 2-methyl-3-ethyl-benzothiazolium | —CH= | 2-methylene-3-ethyl-thiazolidine | ClO₄⁻ | 384 | 55092 | 11 [4] |
| 10 | 2-methyl-3-ethyl-benzothiazolium | —CH= | 2-methylene-3-ethyl-pyrrolidine | ClO₄⁻ | 377 | 66525 | 8 [4] |
| 11 | 2,3,3-trimethyl-1-methyl-indolenium | —CH= | 2-methylene-3-ethyl-thiazolidine | ClO₄⁻ | 386 | 36542 | 17 [4] |
| 12 | 2,3,3-trimethyl-1-methyl-indolenium | —CH= | 2-methylene-3-ethyl-1,3-thiazinane | PF₆⁻ | | | |

-continued

| Example | $R^1$ — structure with $X^2$, m, A | $R^3$, $R^4$, Y, p | B structure with $X^3$, $X^4$, $R^2$, n | An⁻ | $\lambda_{max}$/nm[1] | $\epsilon$/l/mol cm | $\lambda_{1/2}-\lambda_{1/10}$/nm $\Delta\lambda^{2)}$/nm |
|---|---|---|---|---|---|---|---|
| 13 | 2-methyl-3-ethyl-benzothiazolium | —CH= | N-methyl quinoline | Br⁻ | | | |
| 14 | 2-methyl-1-methyl-quinolinium | —CH= | N-ethyl hexahydrobenzothiazole | BF₄⁻ | | | |
| 15 | 2-methyl-N-ethyl-bromo-benz[cd]indolium | C(CN)= | 5-methoxy-3,3-dimethyl-1-methyl indoline | BF₄⁻ | | | |
| 16 | 1,1,2-trimethyl-3-methyl-benz[e]indolium | —CH= | N-ethyl pyrrolidine | ClO₄⁻ | | | |

-continued

| Example | $R^1-X^1$ A (with $X^2$, m) | $R^3, R^4, Y, p$ | B (with $X^3, X^4, R^2$, n) | An⁻ | $\lambda_{max}/nm^{1)}$ | $\epsilon/l/mol\,cm$ | $\lambda_{1/2}-\lambda_{1/10}/nm\ \Delta\lambda^{2)}/nm$ |
|---|---|---|---|---|---|---|---|
| 17 | 2,3,3-trimethyl-1-methyl-3H-indolium | CN, propenyl | 5-chloro-1,3,3-trimethyl-2-methylene-indoline | BF₄⁻ | 501, 526⁶⁾ | 59851 | 38³⁾ |
| 18 | 2,3,3-trimethyl-1-methyl-3H-indolium | CN, propenyl | 5-chloro-1,3,3-trimethyl-2-methylene-indoline | I⁻ | 501, 526⁶⁾ | 74405 | 38³⁾ |
| 19 | 2,3,3-trimethyl-1-methyl-3H-indolium | CN, propenyl | 5-chloro-1,3,3-trimethyl-2-methylene-indoline | B(C₆H₅)₄⁻ | 502, 526⁶⁾ | 46643 | |
| 20 | 5-methoxycarbonyl-1,2,3,3-tetramethyl-3H-indolium | CN, propenyl | 5-methoxycarbonyl-1,3,3-trimethyl-2-methylene-indoline | Cl⁻ | 508, 534⁶⁾ | 59054 | 42³⁾ |

-continued

| Example | $R^1$—$X^1$ (A) $X^2$ $_m$ | $R^3$, $R^4$, $Y$, $p$ | $X^4$ (B) $X^3$—$R^2$ $_n$ | An$^-$ | $\lambda_{max}$/nm[1] | $\epsilon$/l/mol cm | $\lambda_{1/2}$-$\lambda_{1/10}$/nm $\Delta\lambda^{2)}$/nm |
|---|---|---|---|---|---|---|---|
| 21 | | | | Cl$^-$ | 514[6] | 31169 | 52[3] |
| 22 | | | | Cl$^-$ | 512, 534[6] | 69252 | 35[3] |
| 23 | | | | CH$_3$SO$_3^-$ | 549[5] | | |
| 24 | | | | BF$_4^-$ | 549[5] | 126628 | 10[4] |
| 25 | | | | ClO$_4^-$ | 483 | 87150 | 31[3] |

-continued

| Example | $R^1-X^1\overset{A}{\underset{X^2}{\diagdown}}\underset{m}{\diagdown}$ | $\overset{R^3}{\underset{R^4}{\diagdown}}\underset{p}{=}Y$ | $\overset{X^4}{\underset{B}{\diagdown}}\overset{X^3-R^2}{\underset{n}{\diagdown}}$ | An⁻ | $\lambda_{max}$/nm[1] | $\epsilon$/l/mol cm | $\lambda_{1/2}$-$\lambda_{1/10}$/nm $\Delta\lambda^{2)}$/nm |
|---|---|---|---|---|---|---|---|
| 26 | 1,2,3,3-tetramethyl-3H-indolium | pentadienyl | 3-ethyl-2-methylene-thiazolidine | CH₃COO⁻ | 484 | 79950 | 29[3] 10 |
| 27 | 1,2-dimethylquinolinium | pentadienyl | 3-ethyl-2-methylene-thiazolidine | ClO₄⁻ | | | |
| 28 | 1,2,3,3-tetramethyl-3H-indolium | pentadienyl | 3-ethyl-2-methylene-thiazolidine | ClO₄⁻ | | | |
| 29 | methyl 1,2,3,3-tetramethyl-3H-indolium-5-carboxylate | propenyl-imino | 3-methyl-2-methylene-benzothiazoline | CH₃SO₃⁻ | 555 | 152955 | 10[4] |

-continued

| Example | A structure | Middle structure | B structure | An⁻ | $\lambda_{max}$/nm[1] | $\epsilon$/l/mol cm | $\lambda_{1/2}$-$\lambda_{1/10}$/nm | $\Delta\lambda^{2)}$/nm |
|---|---|---|---|---|---|---|---|---|
| 30 | 1,3,3-trimethyl-5-methoxy-3H-indolium | N=CH–CH=CH– | 3-methyl-2-methylene-benzothiazoline | CH₃SO₃⁻ | 539, 570 | | 12[4] | |
| 31 | 1,3,3-trimethyl-5-methoxy-3H-indolium | N=CH–CH=CH– | 3-methyl-2-methylene-benzothiazoline | BF₄⁻ | 539, 570 | 79846 | 12[4] | |
| 32 | 1,3,3-trimethyl-3H-indolium | –CH=CH–CH=CH– | 3-methyl-2-methylene-benzothiazoline | BF₄⁻ | | | | |
| 33 | 1-ethyl-2-methyl-benz[cd]indolium | –C(CN)=CH–CH=CH– | 1,3,3-trimethyl-2-methylene-indoline | PF₆⁻ | | | | |

-continued

| Example | A structure (R¹–X¹) | middle (R³, R⁴, Y) | B structure (X³, X⁴, R²) | An⁻ | $\lambda_{max}$/nm[1) | $\epsilon$/l/mol cm | $\lambda_{1/2}$-$\lambda_{1/10}$/nm $\Delta\lambda^{2)}$/nm |
|---|---|---|---|---|---|---|---|
| 34 | 2-methylquinolinium N-C₂H₅ | pentadienyl | benzothiazole N-CH₂CH₂Ph | I⁻ | 590[7) | 171597 | 14[4) |
| 35 | 2-methylquinolinium N-C₂H₅ | pentadienyl | benzothiazole N-CH₂Ph | I⁻ | 581[7) | 135642 | 18[4) |
| 36 | 2-methylquinolinium N-C₂H₅ | pentadienyl | benzothiazole N-C₂H₅ | I⁻ | 588[7) | 206305 | 19[4) |
| 37 | 1,1,2-trimethyl-benz[e]indolium N-CH₃ | pentadienyl | benzothiazole N-C₂H₅ | BF₄⁻ | | | |

-continued

| Example | R¹—X¹ A X² m | R³ R⁴ Y p | X⁴ B X³ R² n | An⁻ | λmax/nm[1] | ε/l/mol cm | λ1/2-λ1/10/nm | Δλ[2]/nm |
|---|---|---|---|---|---|---|---|---|
| 38 | [indolenine structure with H₃C, CH₃, N⁺—CH₃, naphthalene] | [N=] | [thiadiazole with pyrrolidine, S, N—N, H₃C] | BF₄⁻ | | | | |

[1] in methanol unless indicated otherwise.
[2] Δλ = |λmethylene chloride − λmethanol|
[3] on the short wavelength flank
[4] on the long wavelength flank
[5] in methanol/chloroform 1:1
[6] in acetone
[7] in NMP

Example 39

A 2% strength by weight solution comprising 66.7% by weight of the dye from Example 24 and 33.3% by weight of the dye of the formula

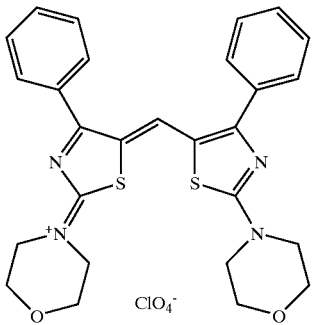

in 2,2,3,3-tetrafluoropropanol was prepared at room temperature. This solution was applied by means of spin coating to a pregrooved polycarbonate substrate. The pregrooved polycarbonate substrate had been produced as a disk by means of injection moulding. The dimensions of the disk and the groove structure corresponded to those customarily used for DVD-Rs. The disk with the dye layer as information carrier was coated with 120 nm of gold and then, on top of the gold layer, 200 nm of SiO by vapour deposition. A UV-curable acrylic coating composition was subsequently applied by spin coating and cured by means of a UV lamp. The disk was tested by means of a dynamic writing test apparatus constructed on an optical tester bench comprising a diode laser ($\lambda$=656 nm) for generating linearly polarized light, a polarization-sensitive beam splitter, a $\lambda/4$ plate and a movably suspended collecting lens having a numerical aperture NA=0.6 (actuator lens). The light reflected from the reflection layer of the disk was taken out from the beam path by means of the abovementioned polarization-sensitive beam splitter and focused by means of an astigmatic lens onto a four-quadrant detector. At a linear velocity V=3.5 m/s and a writing power $P_w$=21 mW, a signal-noise ratio C/N=42 dB was measured. The writing power was applied as an oscillating pulse sequence, with the disk being irradiated alternately for 1 $\mu$s with the abovementioned writing power $P_w$ and for 4 $\mu$s with the reading power $P_r \approx 0.6$ mW. The disk was irradiated with this oscillating pulse sequence until it had rotated once. The marking produced in this way was then read using the reading power $P_r$ and the abovementioned signal/noise ratio C/N was measured.

What is claimed is:

1. Optical data carrier comprising a preferably transparent substrate which may, if desired, have previously been coated with one or more reflection layers and to whose surface a light-writeable information layer, if desired one or more reflection layers and if desired a protective layer or a further substrate or a covering layer have been applied, which can be written on or read by means of blue, red or infrared light, preferably laser light, where the information layer comprises a light-absorbent compound and, if desired, a binder, characterized in that at least one cyanine dye is used as light-absorbent compound, wherein the cyanine dye has the formula (I)

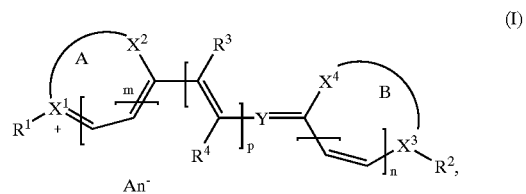

where $X^1$ and $X^3$ represent nitrogen or $X^1$—$R^1$ and $X^3$—$R^2$ represent, independently of one another, S, $X^2$ represents O, S, N—$R^6$, $CR^8$ or $CR^8R^9$, $X^4$ represents O, S, $CR^{10}$ or N—$R^7$, Y represents N, $R^1$, $R^2$, $R^6$ and $R^7$ represent, independently of one another, $C_1$–$C_{16}$-alkyl, $C_3$–$C_6$-alkenyl, $C_5$–$C_7$-cycloalkyl or $C_7$–$C_{16}$-aralkyl, $R^3$, $R^4$ and $R^5$ represent, independently of one another, hydrogen, $C_1$–$C_{16}$-alkyl or cyano or $R^1$ and $R^3$ together represent a —(CH$_2$)$_2$—, —(CH$_2$)$_3$— or —(CH$_2$)$_4$— bridge when m=0 and p>0 or $R^1$ and $R^5$ together represent a —(CH$_2$)$_2$—, —(CH$_2$)$_3$— or —(CH$_2$)$_4$— bridge when m=0 and p=0 or $R^2$ and $R^5$ together represent a —(CH$_2$)$_2$—, —(CH$_2$)$_3$— or —(CH$_2$)$_4$— bridge when n=0, $R^8$, $R^9$ and $R^{10}$ represent, independently of one another, hydrogen or $C_1$–$C_{16}$-alkyl or $CR^8R^9$ represents a bivalent radical of the formula

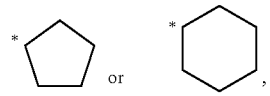

where the two bonds go out from the ring atom marked with an asterisk (*), m and n represent, independently of one another, 0 or 1, p represents 0, 1 or 2, the ring A including $X^1$, $X^2$ and the radical connecting $X^1$ and $X^2$ and the ring B including $X^3$, $X^4$ and the radical connecting $X^3$ and $X^4$ each represent, independently of one another, a five- or six-membered aromatic or pseudoaromatic or partially hydrogenated heterocyclic ring which may contain from 1 to 4 heteroatoms and/or be benzo- or naphtho-fused and/or be substituted by nonionic radicals, where the rings A and B are preferably not identical, and An⁻ represents an anion.

2. Optical data carrier according to claim 1, characterized in that, in the formula (I), the ring A of the formula

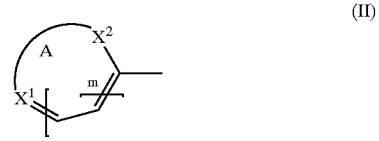

represents benzothiazol-2-yl, thiazol-2-yl, thiazolin-2-yl, benzoxazol-2-yl, oxazol-2-yl, oxazolin-2-yl, benzimidazol-2-yl, imidazol-2-yl, imidazolin-2-yl, pyrrolin-2-yl, 3-H-indol-2-yl, benz[c,d]indol-2-yl, 2- or 4-pyridyl or 2- or 4-quinolyl, where $X^1$ represents N, where the abovementioned rings may each be substituted by $C_1$–$C_6$-alkyl, $C_1$–$C_6$-alkoxy, fluorine, chlorine, bromine, iodine, cyano, nitro, $C_1$–$C_6$-alkoxy-carbonyl, $C_1$–$C_6$-alkylthio, $C_1$–$C_6$-acylamino, $C_6$–$C_{10}$-aryl, $C_6$–$C_{10}$-aryloxy or $C_6$–$C_{10}$-arylcarbonylamino and the ring B of the formula

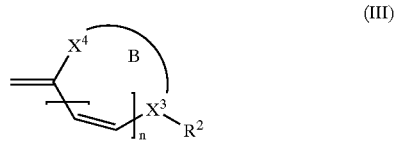

(III)

represents benzothiazol-2-ylidene, thiazol-2-ylidene, thiazolin-2-ylidene, isothiazol-3-ylidene, 1,3,4-thiadiazol-2-ylidene, 1,2,4-thiadiazol-5-ylidene, benzoxazol-2-ylidene, oxazol-2-ylidene, oxazolin-2-ylidene, 1,3,4-oxadiazol-2-ylidene, benzimidazol-2-ylidene, imidazol-2-ylidene, imidazolin-2-ylidene, pyrrolin-2-ylidene, 1,3,4-triazol-2-ylidene, 3H-indol-2-ylidene, benz[c,d]indol-2-ylidene, 2- or 4-pyridyl or 2- or 4-quinolyl, each of which bear the radical $R^2$, which is as defined in claim 2, in $X^3$ which represents N, where the abovementioned rings may each be substituted by $C_1$–$C_6$-alkyl, $C_1$–$C_6$-alkoxy, fluorine, chlorine, bromine, iodine, cyano, nitro, $C_1$–$C_6$-alkoxy-carbonyl, $C_1$–$C_6$-alkylthio, $C_1$–$C_6$-acylamino, $C_6$–$C_{10}$-aryl, $C_6$–$C_{10}$-aryloxy, $C_6$–$C_{10}$-arylcarbonylamino, mono- or di-$C_1$–$C_6$-alkylamino, N—$C_1$–$C_6$-alkyl-N—$C_6$–$C_{10}$-arylamino pyrrolidino, morpholino or piperazino.

3. Optical data carrier according to one or more of claims 1, characterized in that the cyanine dye has the formula (I) in which the ring A and the ring B represent different heterocycles.

4. A method for using cyanine dyes in an information layer of write-once optical data carriers, comprising:

providing the cyanine dyes having an absorption maximum $\lambda_{max1}$ in the range from 340 to 410 nm, wherein the cyanine dye has the formula (I)

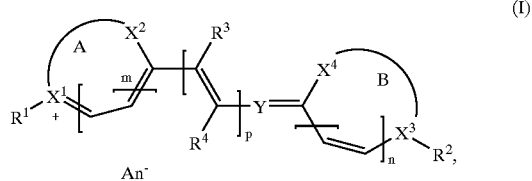

(I)

where $X^1$ and $X^3$ represent nitrogen or $X^1$—$R^1$ and $X^3$—$R^2$ represent, independently of one another, S, $X^2$ represents O, S, N—$R^6$, $CR^8$ or $CR^8R^9$, $X^4$ represents O, S, $CR^{10}$ or N—$R^7$, Y represents N, $R^1$, $R^2$, $R^6$ and $R^7$ represents, independently of one another, $C_1$–$C_{16}$-alkyl, $C_3$–$C_6$alkenyl, $C_5$–$C_7$-cycloalkyl or $C_7$–$C_{18}$-aralkyl, $R^3$, $R^4$ and $R^5$ represent, independently of one another, hydrogen, $C_1$–$C_{16}$-alkyl or cyano or $R^1$ and $R^3$ together represent a —$(CH_2)_2$—, —$(CH_2)_3$— or —$(CH_2)_4$— bridge when m=0 and p>0 or $R^1$ and $R^5$ together represent a —$(CH_2)_2$—, —$(CH_2)_3$— or —$(CH_2)_4$— bridge when m=0 and p=0 or $R^2$ and $R^5$ together represent a —$(CH_2)_2$—, —$(CH_2)_3$— or —$(CH_2)_4$— bridge when n=0, $R^8$, $R^9$ and $R^{10}$ represent, independently of one another, hydrogen or $C_1$–$C_{16}$-alkyl or $CR^8R^9$ represents a bivalent radical of the formula

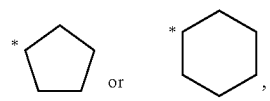

where the two bonds go out from the ring atom marked with an asterisk (*), m and n represent, independently of one another, 0 or 1, p represents 0, 1 or 2, the ring A including $X^1$, $X^2$ and the radical connecting $X^1$ and $X^2$ and the ring B including $X^3$, $X^4$ and the radical connecting $X^3$ and $X^4$ each represent, independently of one another, a five- or six-membered aromatic or pseudoaromatic or partially hydrogenated heterocyclic ring which may contain from 1 to 4 heteroatoms and/or be benzo- or naphtho-fused and/or be substituted by nonionic radicals, where the rings A and B are preferably not identical, and An⁻ represents an anion.

5. A method for using cyanine dyes in an information layer of write-once optical data carriers, comprising:

providing the cyanine dyes having an absorption maximum $\lambda_{max1}$ in the range from 420 to 650 nm, wherein the cyanine dye has the formula (I)

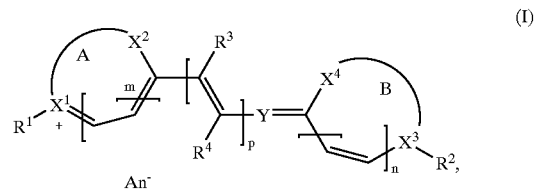

(I)

where $X^1$ and $X^3$ represent nitrogen or $X^1$—$R^1$ and $X^3$—$R^2$ represent, independently of one another, S, $X^2$ represents O, S, N—$R^6$, $CR^8$ or $CR^8R^9$, $X^4$ represents O, S, $CR^{10}$ or N—$R^7$, Y represents N, $R^1$, $R^2$, $R^6$ and $R^7$ represent, independently of one another, $C_1$–$C_{16}$-alkyl, $C_3$–$C_6$-alkenyl, $C_5$–$C_7$-cycloalkyl or $C_7$–$C_{16}$-aralkyl, $R^3$, $R^4$ and $R^5$ represent, independently of one another, hydrogen, $C_1$–$C_{16}$-alkyl or cyano or $R^1$ and $R^3$ together represent a —$(CH_2)_2$—, —$(CH_2)_3$— or —$(CH_2)_4$— bridge when m=0 and p>0 or $R^1$ and $R^5$ together represent a —$(CH_2)_2$—, —$(CH_2)_3$— or —$(CH_2)_4$— m=0 and p>0 or $R^2$ and $R^5$ together represent a —$(CH_2)_2$—, —$(CH_2)_3$— or —$(CH_2)_4$— bridge when n=0, $R^8$, $R^9$ and $R^{10}$ represent, independently of one another, hydrogen or $C_1$–$C_{16}$-alkyl or $CR^8R^9$ represents a bivalent radical of the formula

where the two bonds go out from the ring atom marked with an asterisk (*), m and n represent, independently of one another, 0 or 1, p represents 0, 1 or 2, the ring A including $X^1$, $X^2$ and the radical connecting $X^1$ and $X^2$ and the ring B including $X^3$, $X^4$ and the radical connecting $X^3$ and $X^4$ each represent, independently of one another, a five- or six-membered aromatic or pseudoaromatic or partially hydrogenated heterocyclic ring which may contain from 1 to 4 heteroatoms and/or be benzo- or naphtho-fused and/or be substituted by nonionic radicals, where the rings A and B are preferably not identical, and $An^-$ represents an anion.

6. A method for using cyanine dyes in an information layer of write-once optical data carriers, comprising:

reading and writing on the data carriers by means of blue laser light, wherein the cyanine dye has the formula (I)

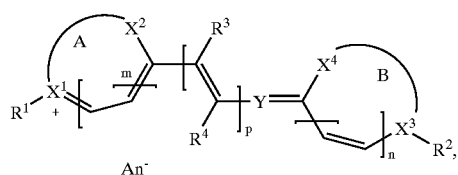

where $X^1$ and $X^3$ represent nitrogen or $X^1$—$R^1$ and $X^3$—$R^2$ represent, independently of one another, S, $X^2$ represents O, S, N—$R^6$, $CR^8$ or $CR^8R^9$, $X^4$ represents O, S, $CR^{10}$ or N—$R^7$, Y represents N, $R^1$, $R^2$, $R^6$ and $R^7$ represent independently of one another, $C_1$–$C_{16}$-alkyl, $C_3$–$C_6$-alkenyl, $C_5$–$C_7$-cycloalkyl or $C_7$–$C_{16}$-aralkyl, $R^3$, $R^4$ and $R^6$ represent, independently of one another, hydrogen, $C_1$–$C_{16}$-alkyl or cyano or $R^1$ and $R^3$ together represent a —$(CH_2)_2$—, —$(CH_2)_3$— or —$(CH_2)_4$— bridge when m=0 and p>0 or $R^1$ and $R^5$ together represent a —$(CH_2)_2$—, —$(CH_2)_3$— or —$(CH_2)_4$— bridge when m=0 and p=0 or $R^2$ and $R^5$ together represent a —$(CH_2)_2$—, —$(CH_2)_3$— or —$(CH_2)_4$— bridge when n=0, $R^8$, $R^9$ and $R^{10}$ represent of one another, hydrogen or $C_1$–$C_{16}$-alkyl or $CR^8R^9$ represents a bivalent radical of the formula

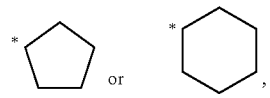

where the two bonds go out from the ring atom marked with an asterisk (*), m and n represent, independently of one another 0 or 1, p represents 0, 1 or 2, the ring A including $X^1$, $X^2$ and the radical connecting $X^1$ and $X^2$ and the ring B including $X^3$, $X^4$ and the radical connecting $X^3$ and $X^4$ each represent, independently of one another, a five- or six-membered aromatic or pseudoaromatic or partially hydrogenated heterocyclic ring which may contain from 1 to 4 heteroatoms and/or be benzo- or naphtho-fused and/or be substituted by nonionic radicals, where the rings A and B are preferably not identical, and $An^-$ represents an anion.

7. A method for using cyanine dyes in an information layer of write-once optical data carriers, comprising:

writing on and reading from the data carriers by means of red laser light, wherein the cyanine dye has the formula (I)

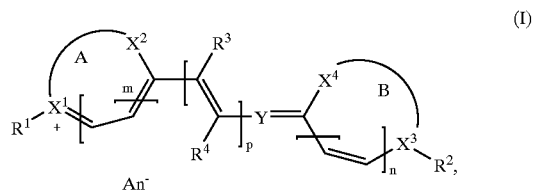

where $X^1$ and $X^3$ represent nitrogen or $X^1$—$R^1$ and $X^3$—$R^2$ represent, independently of one another, S, $X^2$ represents O, S, N—$R^6$, $CR^8$ or $CR^8R^9$, $X^4$ represents O, S, $CR^{10}$ or N—$R^7$, Y represents N, $R^1$, $R^2$, $R^6$ and $R^7$ represent, independently of one another, $C_1$–$C_{16}$-alkyl, $C_3$–$C_6$-alkenyl, $C_5$–$C_7$-cycloalkyl or $C_7$–$C_{16}$-aralkyl, $R^3$, $R^4$ and $R^5$ represent, independently of one another, hydrogen, $C_1$–$C_{16}$-alkyl or cyano or $R^1$ and $R^3$ together represent a —$(CH_2)_2$—, —$(CH_2)_3$— or —$(CH_2)_4$— bridge when m=0 and p>0 or $R^1$ and $R^6$ together represent a —$(CH_2)_2$—, —$(CH_2)_3$— or —$(CH_2)_4$— bridge when m=0 and p=0 or $R^2$ and $R^5$ together represent a —$(CH_2)_2$—, —$(CH_2)_3$— or —$(CH_2)_4$— bridge when n=0, $R^8$, $R^9$ and $R^{10}$ represent, independently of one another, hydrogen or $C_1$–$C_{16}$-alkyl or $CR^8R^9$ represents a bivalent radical of the formula

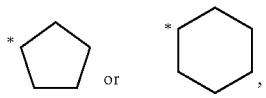

where the two bonds go out from the ring atom marked with an asterisk(*), m and n represent, independently of one another, 0 or 1, p represents 0, 1 or 2, the ring A including $X^1$, $X^2$ and the radical connecting $X^1$ and $X^2$ and the ring B including $X^3$, $X^4$ and the radical connecting $X^3$ and $X^4$ each represent, independently of one another, a five- or six-membered aromatic or pseudoaromatic or partially hydrogenated heterocyclic ring which may contain from 1 to 4 heteroatoms and/or be benzo- or naphtho-fused and/or be substituted by nonionic radicals, where the rings A and B are preferably not identical, and An$^-$ represents an anion.

8. Process for producing the optical data carriers according to claim 1, which is characterized in that a preferably transparent substrate which may, if desired, have previously been coated with a reflection layer is coated with the cyanine dyes of the formula I, if desired in combination with suitable binders and additives and, if desired, suitable solvents, and provided, if desired, with a reflection layer, further intermediate layers and, if desired, a protective layer or a further substrate or a covering layer.

9. Optical data carrier according to claim 1 which can be written on by means of blue, red or infrared, in particular blue or red, light, in particular blue or red laser light.

10. Cyanine dyes of the formula

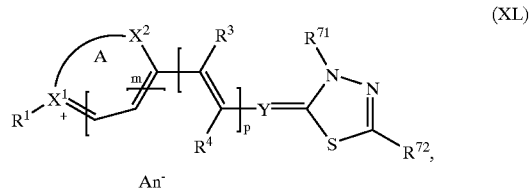

(XL)

where $R^{71}$ represents $C_1$–$C_{16}$-alkyl, $C_3$–$C_5$-alkenyl, $C_5$–$C_7$-cycloalkyl or $C_7$–$C_{16}$-aralkyl, $R^{72}$ represents $C_1$–$C_{16}$-alkoxy, $C_1$–$C_{16}$-alkylthio, di-$C_1$–$C_{16}$-alkylamino, N—$C_1$–$C_{16}$-alkyl-N—$C_6$–$C_{10}$-arylamino, pyrrolidino, piperidino, piperazino or morpholino, Y represents N and the other radicals are as defined in claim 1.

* * * * *